US007512439B1

(12) United States Patent
Farazi

(10) Patent No.: US 7,512,439 B1
(45) Date of Patent: Mar. 31, 2009

(54) IMPLANTABLE DEVICES, AND METHODS FOR USE THEREWITH, FOR PERFORMING CARDIAC AND AUTONOMIC ASSESSMENTS USING PHASE RECTIFIED SIGNAL AVERAGING

(75) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 702 days.

(21) Appl. No.: 11/249,653

(22) Filed: Oct. 12, 2005

(51) Int. Cl.
*A61B 5/04* (2006.01)
*A61N 1/362* (2006.01)

(52) U.S. Cl. ........................................ 600/509; 607/17

(58) Field of Classification Search ........................ None
See application file for complete search history.

(56) References Cited

U.S. PATENT DOCUMENTS

| 6,381,493 | B1 | 4/2002 | Stadler et al. ................... 607/9 |
| 6,487,442 | B1 | 11/2002 | Wood .......................... 600/515 |
| 6,609,023 | B1 | 8/2003 | Fischell et al. ............... 600/515 |
| 2003/0191403 | A1 | 10/2003 | Zhou et al. ................... 600/515 |
| 2004/0186525 | A1 | 9/2004 | Burnes et al. ................. 607/17 |

FOREIGN PATENT DOCUMENTS

WO      WO 03/086187 A1      10/2003

OTHER PUBLICATIONS

Bauer, et al.; "Heart Rate Turbulence"; J Electrocardiol, 2003; 36 Suppl: 89-93.
Barthel, et al.; "Risk Stratification After Acute Myocardial Infaction by Heart Rate Turbulence"; Circulation, 2003; 108:1221.
Mrowka, et al.; "Blunted Arterial Baroreflex Causes 'Pathological' Heart Rate Turbulence"; Am J Physiol Regul Integr Comp Physiol 279: R1171-R1175, 2000; 0363-6119/00.

(Continued)

*Primary Examiner*—Carl H. Layno
*Assistant Examiner*—Jon-Eric C. Morales
(74) *Attorney, Agent, or Firm*—Steven M. Mitchell

(57) ABSTRACT

Provided herein are implantable devices, and methods for use therewith, that perform at least one of a cardiac assessment and an autonomic assessment. An implantable device is used to sense a cardiac electrogram (EGM) signal, and cardiac intervals are measured within a portion of the sensed EGM signal. Anchor points are identified based on the measured cardiac intervals, and for each identified anchor point, a segment of at least three consecutive said cardiac intervals that is generally centered about the anchor point is defined. The segments defined for the anchor points are averaged to produce an average segment. At least one of a cardiac assessment and an autonomic assessment is performed based on the average segment. This can include assessing a patient's autonomic tone based on the average segment, assessing a patients risk of SCD based on the average segment and/or detecting a myocardial ischemic event based on the average segment. This abstract is not intended to describe all of the various embodiments of the present invention.

31 Claims, 8 Drawing Sheets

OTHER PUBLICATIONS

Schmidt, et al.; "Heart Rate Turbulence After Ventricular Premature Beats as a Predictor of Mortality after Acute Myocardial Infarction"; Lancet. Apr. 24, 1999; 353(9162): 1390-1396.

Bonnemeier, et al.; "Reflex Cardiac Activity in Ischemia and Reperfusion: Heart Rate Turbulence in Patients Undergoing Direct Percutaneous Coronary Intervention for Acute Myocardial Infarction"; Circulation 2003; 108: 958-964.

Watanabe, et al.; "Effects of Ventricular Premature Stimulus Coupling Interval on Blood Pressure and Heart Rate Turbulence"; Circulation 2002; 106: 325-330.

Wichterle, et al.; "Mechanisms Involved in Heart Rate Turbulence"; Card Electrophysol Rev. Sep. 2002; 6(3) 262-266.

FIG. 3A Identification of anchor points
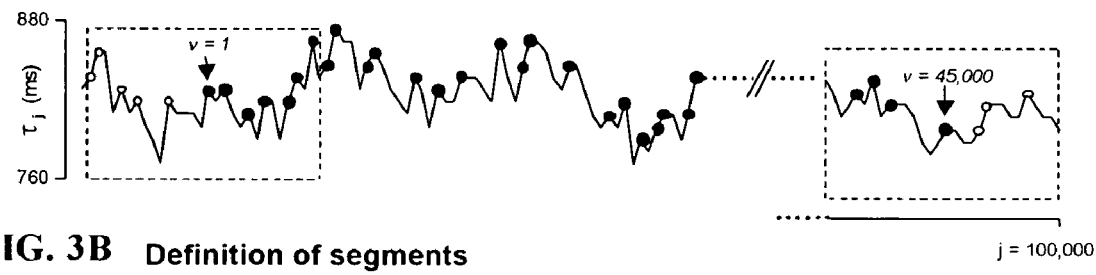
FIG. 3B Definition of segments
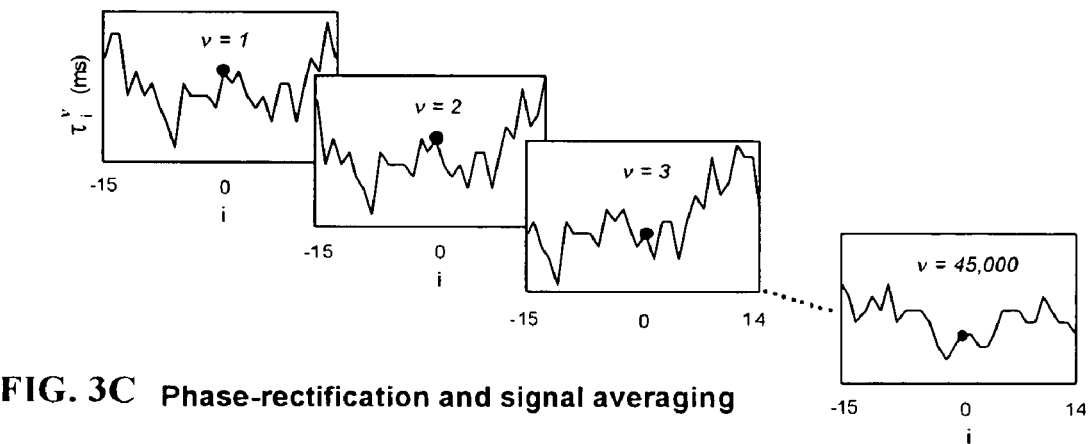
FIG. 3C Phase-rectification and signal averaging
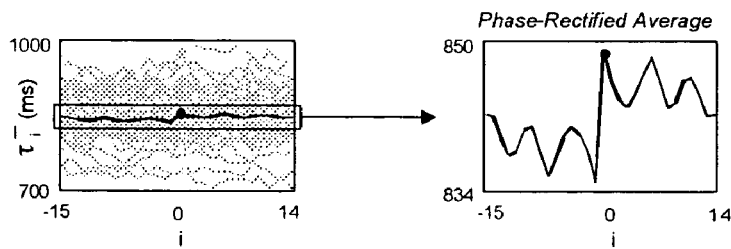

IMPLANTABLE DEVICES, AND METHODS FOR USE THEREWITH, FOR PERFORMING CARDIAC AND AUTONOMIC ASSESSMENTS USING PHASE RECTIFIED SIGNAL AVERAGING

FIELD OF THE INVENTION

The present invention generally relates to an implantable cardiac device that can monitor a patient's heart. The present invention more particularly relates to such an implantable device capable of performing at least one of a cardiac assessment and an autonomic assessment.

BACKGROUND

Recent publications have demonstrated that use of what is referred to as "Phase Rectified Signal Averaging" (PRSA), also known as Heart Rate Harmony (HRH), is superior to using standard deviation of normal RR intervals (SDNN) and left ventricular ejection fraction (LVEF) for prediction of late mortality after a patient has experienced an acute myocardial infarction (AMI). Holter recordings were obtained for a training sample of patients that survived an AMI. PRSA was then used to analyze the Holter recordings of the patients, to thereby predict which patients would experience late mortality (i.e., not survive) and which patient's would not experience later mortality (i.e., survive). Without elaboration, one such publication suggested that the PRSA method may also be proposed for a variety of other applications.

BRIEF SUMMARY OF THE INVENTION

Embodiments of the present invention relate to implantable devices, and methods for use therewith, that perform at least one of a cardiac assessment and an autonomic assessment. An implantable device is used to sense a cardiac electrogram (EGM) signal, and cardiac intervals are measured within a portion of the sensed EGM signal. Anchor points are identified based on the measured cardiac intervals, and for each identified anchor point, a segment of at least three consecutive said cardiac intervals that is generally centered about the anchor point is defined. The segments defined for the anchor points are averaged to produce an average segment. At least one of a cardiac assessment and an autonomic assessment is performed based on the average segment. This can include assessing a patient's autonomic tone based on the average segment, assessing a patients risk of sudden cardiac death (SCD) based on the average segment and/or detecting a myocardial ischemic event based on the average segment.

In accordance specific embodiments, a metric of a central wavelet of the average segment is determined, and the determined metric is compared to one or more threshold to thereby assess a patient's autonomic tone. Additionally or alternatively, a time constant of the average segment is determined, and the determined time constant is compared to one or more threshold to thereby assess a patient's autonomic tone. In still other embodiments, a slope of the average segment is determined, and the determined slope is compared to one or more threshold to thereby assess a patient's autonomic tone. The assessed autonomic tone for the patient can be compared with a previously assessed autonomic tone for the patient to monitor changes in autonomic tone. In one embodiment, the assessed autonomic tone for the patient is compared with a threshold corresponding to an imminent risk of an arrhythmia, to determine whether the patient is at risk of an imminent arrhythmia. Cardiac therapy can then be delivered, in response to a determination that the patient is at risk of an imminent arrhythmia.

In accordance specific embodiments, a metric of a central wavelet of the average segment is determined, and the determined metric is compared to one or more threshold to thereby assess a patient's risk of sudden cardiac death (SCD). Additionally or alternatively, a time constant and/or slope of the average segment is determined, and the determined time constant and/or slope is compared to one or more corresponding threshold to thereby assess a patient's risk of SCD. The assessed risk of SCD can be compared with a previously assessed risk of SCD for the patient to monitor changes in the patient's risk of SCD. In one embodiment, the assessed risk of SCD for the patient is compared with a threshold corresponding to an imminent risk of an arrhythmia, to determine whether the patient is at risk of an imminent arrhythmia. Cardiac therapy can then be delivered, in response to a determination that the patient is at risk of an imminent arrhythmia.

In accordance specific embodiments, a temporary decrease in a metric of a central wavelet of an average deceleration segment (or a temporary increase in a metric of a central wavelet of an average acceleration segment) is recognized as being indicative of a myocardial ischemic event. Additionally or alternatively, a temporary decrease in a time constant and/or a temporary increase in a slope of the average segment is recognized as being indicative of a myocardial ischemic event. Ischemic events detected over time can then be used to assess a patient's ischemic burden.

This description is not intended to be a complete description of, or limit the scope of, the invention. Alternative and additional features, aspects, and objects of the invention can be obtained from a review of the specification, the figures, and the claims.

BRIEF DESCRIPTION OF THE DRAWINGS

FIGS. 3A-3C are useful for explaining phase rectified signal averaging techniques. FIG. 3A illustrates an exemplary graph of beat numbers versus RR intervals that is produced from a portion of a cardiac signal. FIG. 3B illustrates exemplary segments of the cardiac signal that are centered around anchor points that are identified based on the graph of FIG. 3A. FIG. 3C is a graph illustrating an average of the segments illustrated in FIG. 3B.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Figure 1:
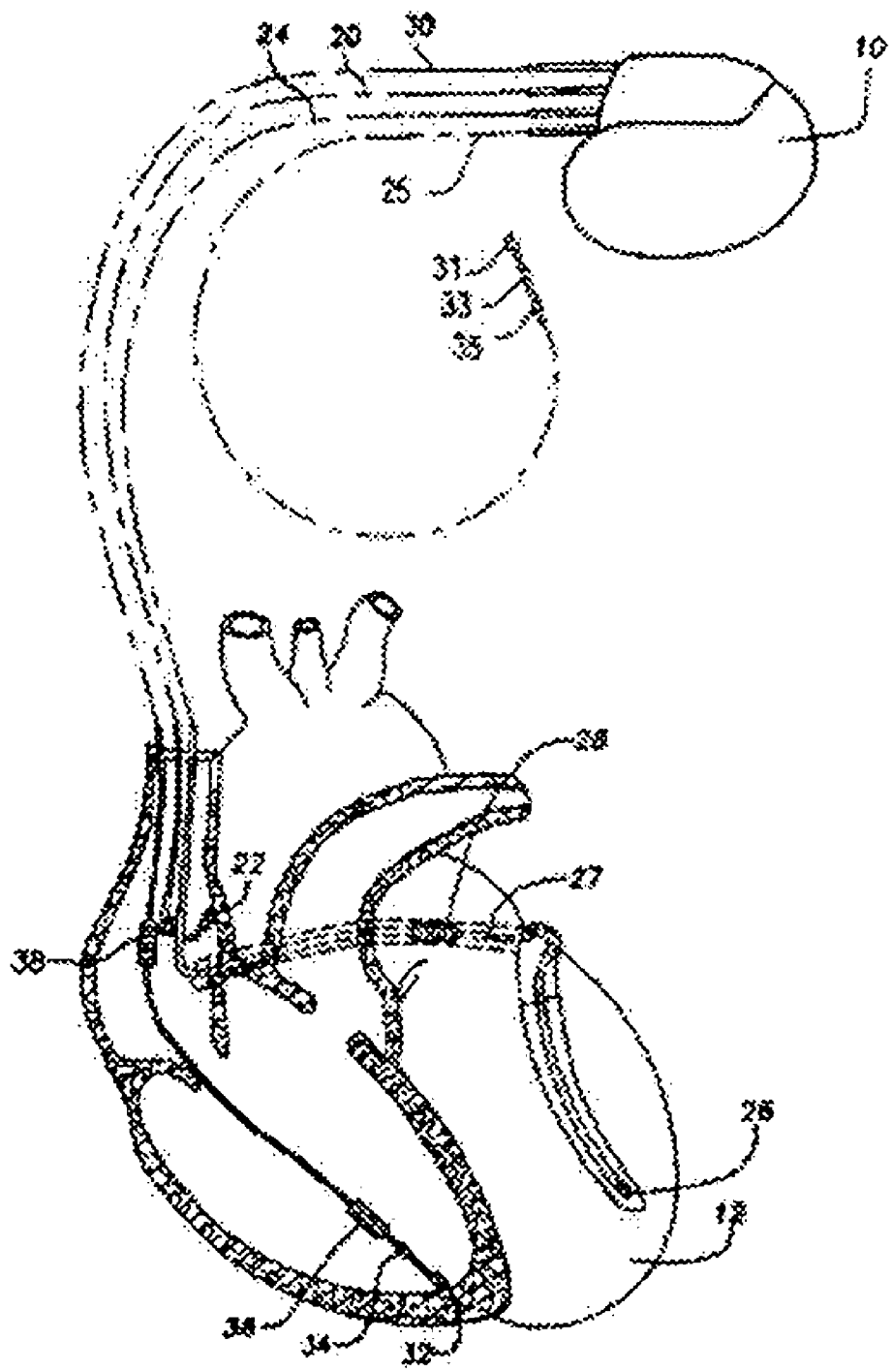
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
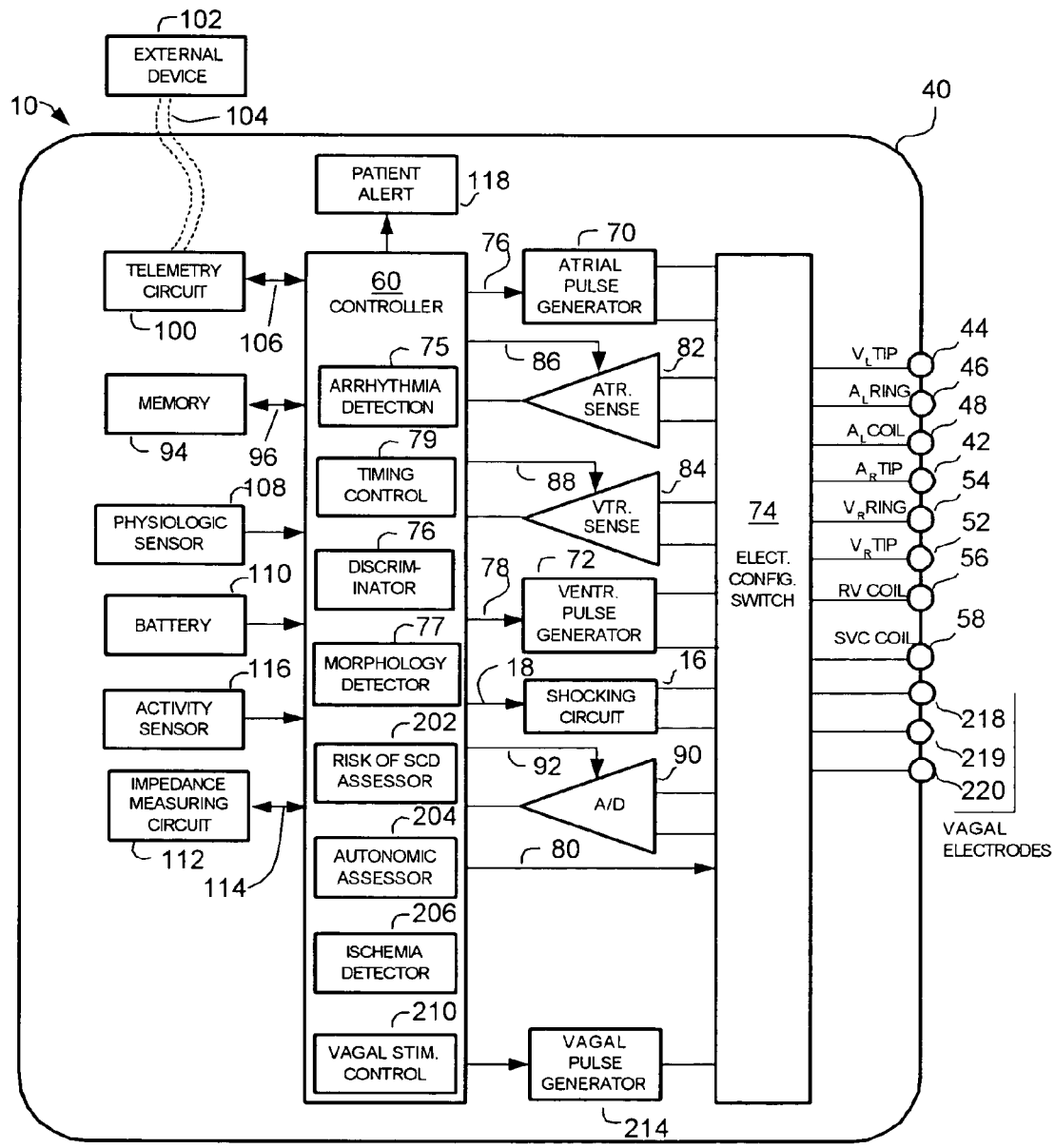
FIG. 2 is a functional block diagram of an exemplary ICD that can provide cardioversion, defibrillation, and pacing stimulation in four chambers of a heart, and performing cardiac and autonomic assessments, in accordance with embodiments of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply is used herein to refer to any implantable cardiac device. FIGS. 1 and 2 illustrate such an environment in which embodiments of the present invention can be used.

Referring first to FIG. 1, an exemplary implantable device 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, implantable device 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, implantable device 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The implantable device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, the implantable device 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of the implantable device 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of the implantable device 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of the implantable device 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the implantable device 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, the implantable device 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting T-wave alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of the implantable device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of the implantable device 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of the implantable device 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

The implantable device 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within the implantable device 10, it is to be understood that physiologic sensor 108 may also be external to the implantable device 10, yet still be implanted within or carried by the patient. More specifically, sensor 108 can be located inside the implantable device 10, on the surface of the implantable device 10, in a header of the implantable device 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The implantable device 10 may also include a magnet detection circuitry (not shown), coupled to microcontroller 60. It is the purpose of the magnet detection circuitry to detect when a magnet is placed over the implantable device 10. A clinician may use the magnet to perform various test functions of the implantable device 10 and/or to signal microcontroller 60 that the external programmer 102 is in place to receive or transmit data to microcontroller 60 through telemetry circuit 100.

As further shown in FIG. 2, the implantable device 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where the implantable device 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

The implantable device 10 additionally includes a battery 110, which provides operating power to a load that includes all of the circuits shown in FIG. 2.

In accordance with embodiments of the present invention, the implantable device 10 includes modules 202, 204 and 206 which, as described in more detail below, can respectively assess a patient's risk of sudden cardiac death (SCD), assess a patient's autonomic tone, and detect myocardial ischemic events. Each module 202, 204 and 206 can be implemented within the microcontroller 60, as shown in FIG. 2. Thus, such modules can be implemented by software, firmware, or combinations thereof. It is also possible that all, or portions, of modules 202, 204 and 206 can be implemented using hardware. Further, it is possible that all, or portions, of modules 202, 204 and 206 be implemented external to the microcontroller 60. Additionally, as will be appreciated from the description set forth below, because many of the features performed by modules 202, 204 and 206 are similar, such modules can be combined.

In an embodiment, one or more of the modules 202, 204 and 206 triggers data acquisition circuit 90 and timing control circuit 79 to sense an EGM signal. The modules use the sensed EGM signal to assess a patient's risk of sudden cardiac death (SCD), assess a patient's autonomic tone, and/or detect myocardial ischemic events, in manners described in detail below. Modules 202, 204 and/or 206 can also trigger implantable device 10 to respond appropriately when certain assessments or detections are made, as will be explained in more detail below. Additionally, in conjunction with a telemetry circuit 100, the modules 202, 204 and/or 206 can be configured to deliver status information, relating to the patient's risk of SCD, autonomic tone and/or ischemic burden, to an external device 102 through an established communication link 104. Such modules may also trigger a patient or physician alert in response to detecting a high risk of SCD, an extremely low parasympathetic tone, an immanent risk of an arrhythmia, a high ischemic burden, etc. For example, a patient alert 118, which produces a vibratory or auditory alert, may be triggered.

As mentioned above, it has been recently demonstrated that Phase Rectified Signal Averaging (PRSA), also known as Heart Rate Harmony (HRH), is superior to techniques that use SDNN and left ventricular ejection fraction (LVEF) for prediction of late mortality after a patient has experienced an acute myocardial infarction (AMI). To support such findings, Holter recordings were obtained for a training sample of patients that survived an AMI. PRSA was then used to analyze the Holter recordings of the patients, to thereby predict which patients would experience late mortality (i.e., not survive) and which patient's would not experience later mortality (i.e., survive). Without elaboration, one such publication suggested that the PRSA method may also be proposed for a variety of other applications.

The inventor or the present invention believes that PRSA techniques can be used by implantable cardiac devices, to perform various cardiac and autonomic assessments, even in patients that have never experienced an AMI. More specifically, the inventor of the present invention believes that PRSA techniques can be used to assess a patients risk of sudden cardiac death (SCD) and track changes in a patients risk of SCD. The inventor also believes that PRSA techniques can be used to detect an imminent risk of an arrhythmia, and to a trigger cardiac therapy in response to such a detection. Additionally, the inventor believes that PRSA techniques can be used to assess a patient's autonomic tone, as well as monitor changes in autonomic tone. Further, the inventor believes that PRSA techniques can be used to detect myocardial ischemic events. The inventor also believes that PRSA techniques can be used to assess whether a patient should be upgraded from a simple implantable monitor or pacemaker to an implantable cardio defibrillator (ICD). Each of these embodiments are discussed in additional detail below.

For completeness, prior to discussing the specific embodiments just set forth above, PRSA techniques will first be generally described. The first step in this technique is to obtain a cardiac signal from a patient of interest. Prior publications teach using an ambulatory Holter recording device to obtain an ECG signal from a patient that has survived an acute myocardial infarction (AMI), and then analyzing the recorded ECG signal for the purpose predicting late mortality after the AMI. In contrast, in accordance with embodiments of the present invention, rather than obtaining an ECG signal from an ambulatory device, an implantable cardiac device is used to sense a cardiac electrogram (EGM) signal using implanted electrodes that are endocardial (inside the heart), epicardial (on the surface of the heart) and/or subcutaneous (under the skin, but not in contact with the heart). Accordingly, in one embodiment the cardiac electrogram is an intra-cardiac electrogram (IEGM) signal, but embodiments are not limited thereto. Measures of RR intervals are then obtained for a window of the cardiac signal. An exemplary plot of 100,000 RR intervals is shown in FIG. 3A, with the horizontal axis indicating beat number, and the vertical axis indicating the RR intervals in milliseconds (ms). The next step is to identify each RR interval that is longer than the immediately preceding RR interval as a positive anchor point. The positive anchor points are shown as solid black circles, in FIG. 3B, with 45,000 anchor points being identified. Then, for each positive anchor point, a segment (also referred to as a "window") of N consecutive RR intervals is defined, with the segment being generally centered about the positive anchor point. Thus, if 45,000 anchor points are identified, then 45,000 segments or windows are defined. FIG. 3B shows the first three segments, and the last segment, with each segment including 30 consecutive RR intervals in this example. In each segment or window, the anchor point is numbered "0" on the horizontal axis, with the segment being generally centered about the anchor point. A next step is to ensemble average the segments created for the positive anchor points to produce an average segment, which has been referred to as an average positive phase-rectified signal. This can be done by lining up all the segments, such that the anchor points are lined up, and then averaging the lined up RR intervals from each segment. In the left most graph of FIG. 3C, the numerous light gray lines are illustrative of the segments that are created for each of the positive anchor points, and the dark line in the center illustrates the average segment. The right most graph of FIG. 3C is a more focused view of the average segment.

Figure 4A:
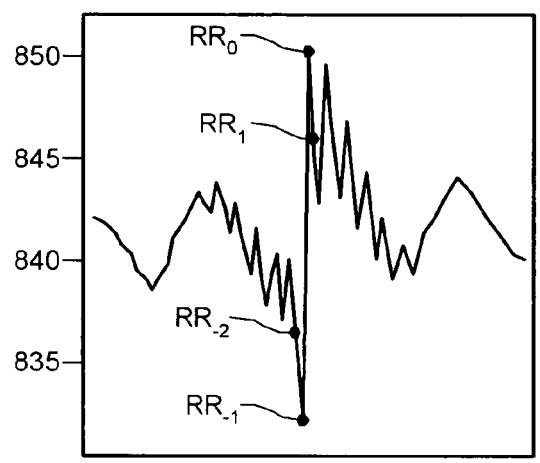
FIGS. 4A and 4B illustrate exemplary average segments.
Figure 4B:
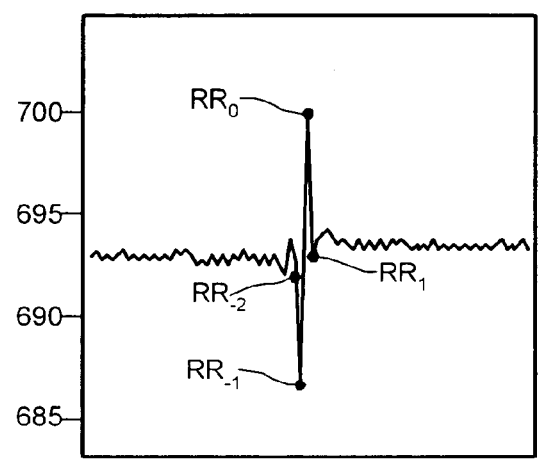

As mentioned above, prior publications have used PRSA based on ambulatory Holter recordings for prediction of late mortality after acute myocardial infarction (AMI). To do this, the PRSA was quantified based on the amplitude of the central wavelet (C) of the average segment, which can be estimated using the equation: $C=(RR_0+RR_1)-(RR_{-1}+RR_{-2})$. The graph of FIG. 4A shows points $RR_0$, $RR_1$, $RR_{-1}$ and $RR_{-2}$ for an exemplary patient that did not experience later mortality after AMI (i.e., for a survivor). The graph of FIG. 4B shows points $RR_0$, $RR_1$, $RR_{-1}$ and $RR_{-2}$ for an exemplary patient that experienced late mortality after AMI (i.e., for a non-survivor). Notice how the amplitude of C is significantly greater for the survivor, than for the non-survivor.

It is the inventor's understanding that prior publications have only explained how PRSA techniques can be used with patients that have experienced an AMI. Additionally, it is the inventor's understanding that prior publications have only applied PRSA techniques to ECG signals that were recorded using ambulatory Holter recording devices. Further, the inventor believes that prior publications have limited the use of PRSA techniques for use in predicting late mortality in survivors of AMI, based on ECG signals that were recorded over a relatively short period of time (e.g., two days).

A unique feature of embodiments of the present invention is that PRSA techniques are not limited to use with patients that have experienced an AMI. Another unique feature of specific embodiments of the present invention is that PRSA is applied to EGM signals that are sensed endocardially, epicardially and/or subcutaneously by an implantable cardiac device. An additional unique feature of specific embodiments of the present invention is that PRSA techniques are repeatedly (e.g., continuously or periodically) used by an implantable device to monitor changes in a patients cardiac and/or autonomic condition. A further unique feature of specific embodiments of the present invention is that PRSA is used for real-time cardiac assessment and feedback. For example, in accordance with specific embodiments of the present invention, PRSA techniques are used to assess a patient's risk of sudden cardiac death (SCD) and to track changes in a patients risk of SCD. Specific embodiments of the present invention also use PRSA techniques to detect an imminent risk of an arrhythmia, and to a trigger cardiac therapy in response to such a detection. Additionally, specific embodiments of the present invention use PRSA to assess a patient's autonomic tone, as well as monitor changes in autonomic tone. Further, embodiments of the present invention use PRSA techniques to detect myocardial ischemic events. In still other embodiments, PRSA techniques are used to assess whether a patient should be upgraded from an implantable monitor are pacemaker to a implantable cardio defibrillator (ICD). Further details of these unique features of the various embodiments of the present invention are discussed below.

Sudden Cardiac Death

Sudden cardiac death (SCD), also known as cardiac arrest, is generally defined as a sudden, abrupt loss of heart function in a person who may or may not have been diagnosed with heart disease, but in whom the time and mode of death occur unexpectedly. SCD is not the same as an acute myocardial infarction (AMI), also known as a heart attack, which is the result of a blockage in an artery which feeds the heart, thereby staving a part of the heart of oxygen. In survivors of an AMI, the part of the heart that has been starved of oxygen may be damaged beyond repair, but the heart can typically still beat effectively. In contrast, SCD is typically caused by a ventricular fibrillation (VF), where the lower chamber of the heart quivers instead of pumping in an organized rhythm, and the VF typically does not return to normal by itself, so the condition requires immediate intervention. Ventricular tachycardia (VT) can also lead to SCD.

While it is possible that a patient that has experienced an AMI may be at an increased risk of SCD, it is not necessarily the case. Further, there are many patients that have never experienced an AMI, yet are at an increased risk of SCD. Accordingly, where a patient has an implantable cardiac device (e.g., a monitor, pacemaker or ICD) implanted within them, for whatever reason, it would be useful if the implantable device can monitor the patient's risk of SCD, so that an appropriate response can be triggered as necessary. Embodiments of the present invention perform such risk monitoring using PRSA techniques, as will be explained with reference to FIG. 5. More generally, FIG. 5 is used to describe methods for use with an implantable system, for assessing a patient's risk of SCD, in accordance with specific embodiments of the present invention.

Figure 5:
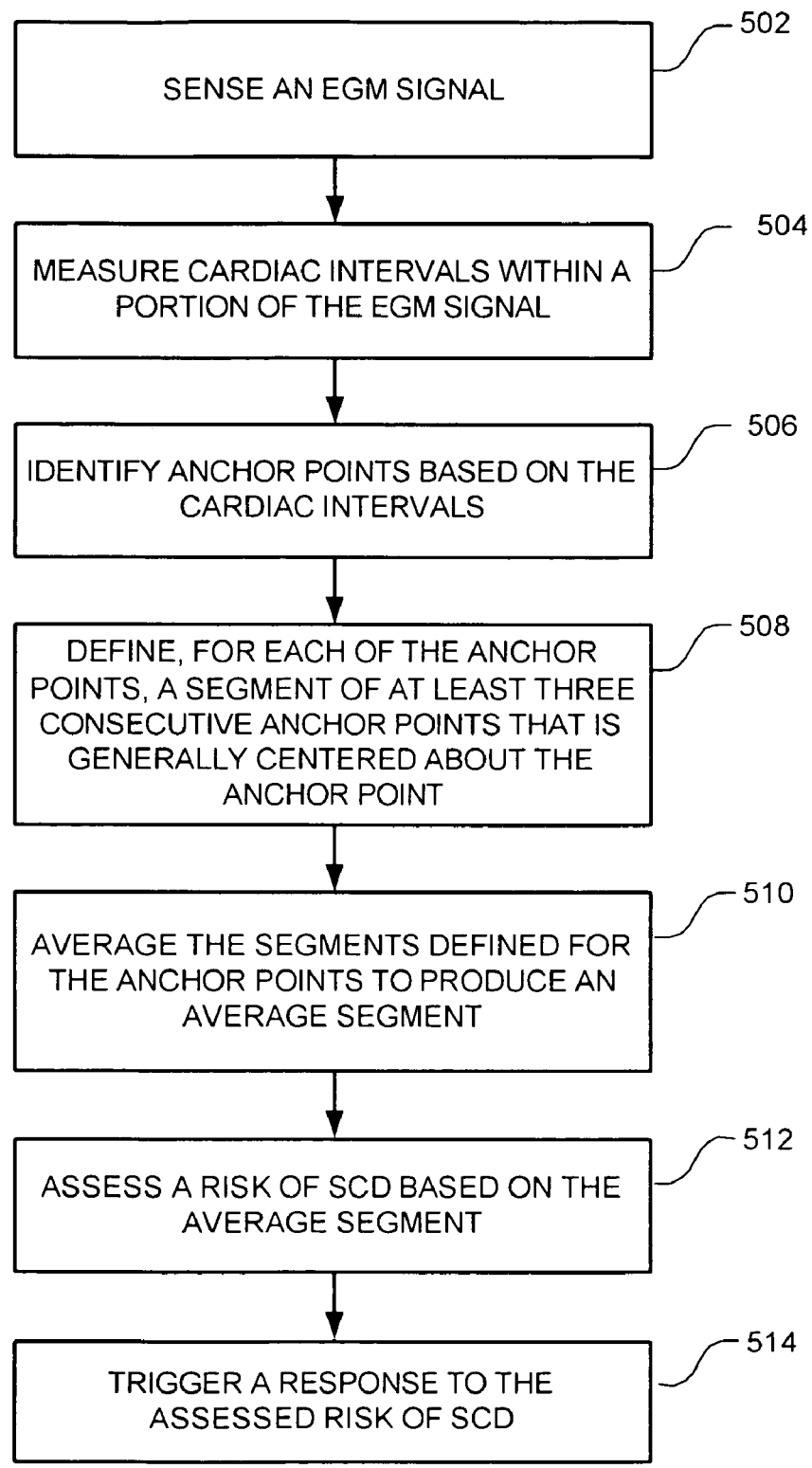
FIG. 5 is a high-level flow diagram that is useful for describing embodiments of the present invention that relate to assessing a patient's risk of SCD.

In FIG. 5, a flow diagram is shown describing an overview of the operation and novel features implemented in one embodiment of the device 10. In this flow diagram, and the other flow diagrams described herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of the stimulation device. Those skilled in the art may readily write such a control program based on the flow diagrams and other descriptions presented herein.

Referring to FIG. 5, at a step 502 a cardiac electrogram (EGM) signal is sensed using an implantable device (e.g., a monitor, pacemaker or ICD). At a step 504, cardiac intervals are measured within a portion of the sensed EGM signal. In specific embodiments, step 504 can include detecting cardiac events in the portion of the EGM signal, and then measuring cardiac intervals based on the detected cardiac events. For example, each cardiac cycle of an EGM signal includes a P-wave that is a normally small positive wave caused by the beginning of a heart beat and representing atrial depolarization. Following the P-wave there is a portion which is substantially constant in amplitude. The QRS complex (representing ventricular depolarization) of the EGM then normally occurs after the substantially constant portion, beginning with a Q-wave that is normally a small negative deflection, which is then immediately succeeded by the R-wave that is a rapid positive deflection. Following the R-wave, the QRS complex is completed with an S-wave that is generally characterized by a small positive inflection in the EGM signal. Following the S-wave is a T-wave (representing ventricular repolarization), which is separated from the S-wave by the ST-segment. The cardiac intervals that are measured at step 504 can be, e.g., RR intervals, PP intervals or PR intervals. An exemplary plot of measured RR intervals versus beat numbers is shown in FIG. 3A, which was discussed above.

At a step 506, anchor points are identified based on the measured cardiac intervals. In one embodiment, step 506 includes identifying each cardiac interval that is longer than the immediately preceding cardiac interval as a positive anchor point. Referring again to FIG. 3A, the solid black circuits illustrate exemplary positive anchor points. Alternatively, or additionally, step 506 can include identifying each cardiac interval that is shorter than the immediately preceding cardiac interval as a negative anchor point.

At a step 508, a segment (e.g., window) of at least three consecutive cardiac intervals is defined for each identified anchor point, where the segment is generally centered about the anchor point. For example, as discussed above, FIG. 3B shows the first three segments, and the last segment, that are defined for 45,000 identified positive anchor points, with each segment including 30 consecutive RR intervals. In FIG. 3B, in each segment or window, the anchor point is numbered "0" on the horizontal axis, with the segment being generally centered about the anchor point. It is noted, however, that anchor point need not be as centered as shown in FIG. 3B. For example, if each segment includes 10 consecutive RR intervals, the anchor point of each segment could be the third RR interval, with two RR intervals prior to the anchor point and seven RR intervals after the anchor point, within the segment.

Where segments are centered around positive anchor points (indicative of cardiac intervals that are longer than the immediately preceding cardiac interval), the segments may be referred to hereafter as deceleration segments. This is because a lengthening of a cardiac interval (e.g., RR interval) is indicative of a deceleration in heart rate. Where segments are centered around negative anchor points (indicative of cardiac intervals that are shorter than the immediately preceding cardiac interval), the segments may be referred to hereafter as deceleration segments. This is because a shortening of a cardiac interval (e.g., RR interval) is indicative of an acceleration in heart rate.

At a step 510, the segments defined for the anchor points are averaged (e.g., ensemble averaged) to produce an average segment. If the anchor points identified at step 506 are positive anchor points, then step 510 results in an average deceleration segment. An exemplary average deceleration segment is shown in FIG. 3C, was discussed above. If the anchor points identified at step 506 are negative anchor points, then step 510 results in an average acceleration segment.

At a step 512, a patient's risk of sudden cardiac death (SCD) is assessed based on the average segment. At a step 514, one or more response is triggered based on the assessed the risk of SCD, if appropriate.

The assessing of a patient's risk of SCD at step 512 can be accomplished in various manners, as will now be explained. In accordance with certain embodiments of the present invention, a patient's risk of SCD is based on characteristics or metrics of the central wavelet (C) of the average segment, where the central wavelet is the wavelet of maximum amplitude of the average segment. For example, the risk of SCD can be based on the amplitude of the central wavelet (C), which can be estimated using the equation: $C=(RR_0+RR_1)-(RR_{-1}+RR_{-2})$. In this embodiment, if the anchor points identified at step 506 are positive anchor points (resulting in an average deceleration segment at step 510), then the amplitude of the central wavelet is inversely proportional to the risk of SCD. In other words, the greater the amplitude of the central wavelet, the less risk of SCD; and the lower the amplitude of the central wavelet, the greater the risk of SCD. Thus, referring back to FIGS. 4A and 4B, FIG. 4A would be representative of a low risk of SCD, and FIG. 4B would be representative of a high risk of SCD. An alternative equation that can be used to characterize the central wavelet is $(RR_0+RR_1)/2-(RR_{-1}+RR_{-2})/2$. In still another embodiment, the central wavelet can be simply characterized by $RR_0$. Where the cardiac intervals are PP intervals or PR intervals, instead of RR intervals, measures of PP intervals or PR intervals can be substituted in the equations discussed above. In contrast, if the anchor points identified at step 506 are negative anchor points (resulting in an average acceleration segment at step 510), then the amplitude of the central wavelet is proportional to the risk of SCD, in that: the greater the amplitude of the central wavelet, the greater the risk of SCD; and the lower the amplitude of the central wavelet, the less the risk of SCD.

In the above described embodiments, increases in the metric of the central wavelet are indicative of reductions in the patient's risk of SCD, and decreases in the metric of the central wavelet are indicative of increases in the patient's risk of SCD. The above description provides just a few example metrics of the central wavelet of the average segment that can be measured. Based on the description herein, one of ordinary skill in the art will appreciate that uses of other metrics are also within the scope of the present invention.

In still another embodiment, a forward time constant of the average segment can be determined, which is representative of the amount of time it takes the average segment to go from its peak to a baseline value. Other definitions of time constant may also be used. For example, the time constant may be defined as the time it takes the average segment to go from its peak to 37% of the peak value. The time constant (or a normalized version thereof) can then be compared to one or more threshold to specify a risk of SCD. For example, referring to FIGS. 4A and 4B, it can be appreciated that the forward time constant for the average segment of FIG. 4A is significantly greater than the forward time constant for the average segment of 4B. Similarly, a backward time constant of the average segment can be determined, which is representative of the amount of time that it takes for the average segment to go from a baseline value to its peak. Referring again to FIGS. 4A and 4B, it can be appreciated that the backward time constant for the average segment of FIG. 4A is significantly greater than the backward time constant for the average segment of 4B. In these embodiments, increases in forward and/or backward time constant are indicative of reductions in the patient's risk of SCD, and decreases in the forward and/or backward time constant are indicative of increases in the patient's risk of SCD. This should be the same regardless whether the anchor points identified at step 506 are positive anchor points (resulting in an average deceleration segment at step 510), or negative anchor points (resulting in an average acceleration segment at step 510).

In still another embodiment, the forward slope of a best fit line can be determined, which is representative of the amount of time it takes the average segment to go from a baseline value to its peak, or a backward slope can be determined, which is representative of the amount of time it takes the average segment to go from its peak to a baseline value. For example, at least 3 (and preferably at least 5) points can be used to specify a best fit line, from which a forward and/or backward slope can be determined. The slope (or a normalized version thereof) can then be compared to one or more threshold to specify a risk of SCD. For example, referring to FIGS. 4A and 4B, it can be appreciated that the magnitudes of the forward and backward slopes for the average segment of FIG. 4A are less than the magnitudes of the forward and backward the slopes of the average segment of 4B. In these embodiments, increases in forward and/or backward slope are indicative of increases in the patient's risk of SCD, and decreases in the forward and/or backward slopes are indicative of decreases in the patient's risk of SCD. This should be the same regardless whether the anchor points identified at step 506 are positive anchor points (resulting in an average deceleration segment at step 510), or negative anchor points (resulting in an average acceleration segment at step 510).

In each of the above embodiments, the measurements of the central wavelet, time constant or slope can be used raw, or they can be normalized before they are used. Such normalization can be achieved, e.g., by dividing a raw value by a normalization value. The normalization value can be specific to the patient, and determined and set, e.g., at the time the cardiac device is implanted. Alternatively, the normalization value can be set based on a broad patient population. A benefit of normalizing measurements is that if measurements are to be compared to one or more threshold, then the thresholds can be defined for a patient population (as opposed to having to specify thresholds for each patient).

Each of the above metrics (of the central wavelet, time constant and/or slope) that are determined from an average segment (before or after normalization) can be compared to one or more corresponding threshold to determine a risk of SCD. For example, if a single threshold is used, then a risk of SCD can be classified as low if the metric is above the threshold, or high if the metric is below the threshold. If two thresholds are used, then the risk of SCD can be classified as high, medium or low. Of course, more thresholds can be used if the desire is to provide more levels of risk. It is also within the scope of the present invention that a threshold could be specified that is indicative of an imminent risk of an arrhythmia. For example, this can be accomplished by specifying an threshold indicative of an extremely small central wavelet or a very short time constant. It is also within the scope of the present invention that a threshold could be specified that, when crossed, is indicative that a patient should be upgraded to a device capable of delivering shock therapy, such as an ICD.

Since embodiments of the present invention are intended to be used with a chronically implanted device, each time the device assesses a risk of SCD (or measures a metric indicative of the risk of SCD), the device can store information indicative of the risk so that it can be compared with one or more previously assessed risk of SCD and/or one or more risk of SCD assessed in the future, thereby enabling the device to track changes in the patient's risk of SCD. In other words, steps 502-512 can be repeated from time to time (e.g., continually, once a day, once a week or once a month, etc.) so that changes in a patient's risk of SCD can be monitored. For a specific example, an assessed risk of SCD for a patient can be compared with a previously assessed risk of SCD for the patient to determine whether there has been an increase or a decrease in the patient's risk of SCD. For example, where the amplitude of the central wavelet and/or the forward time constant is being used to assess the risk of SCD, an increase in the amplitude of the central wavelet and/or the forward time constant would be indicative of a decrease in the risk of SCD, and a decrease in the amplitude of the central wavelet and/or the forward time constant would be indicative of an increase in the risk of SCD. It is also within the scope of the present invention that such information can be used when determining whether a patient should be upgraded to a device capable of delivering shock therapy, such as an ICD.

The portion of the sensed EGM signal, within which cardiac intervals are measured at steps 504, can be specified by a sliding window. This would be a useful way for using the embodiments of the present invention on a generally continuous basis, to thereby track changes in risk of SCD (or changes in autonomic tone, or to detect transient ischemic events, as discussed below). For example, such a sliding window (and thus, the "portion" of the sensed EGM signal from which measurements are made at step 504), can be a 500 beat long sliding window. The next sliding window can be simply shifted over a single beat, or preferably a more significant distance, such as 50 beats, to avoid almost complete overlap of consecutive sliding windows/portions of the EGM signal that are analyzed. It is also possible that consecutive sliding windows do not overlap at all (e.g., consecutive 500 beat windows can be separated by 50 beats).

As mentioned above, at step 514 one or more response can be triggered based on the assessed risk of SCD. In accordance with an embodiment of the present invention, step 514 can involve storing information related to a risk of SCD for later retrieval and/or transmission to a physician or other clinician. This can include, for example, storing metrics of the average segment that are indicative of a risk of SCD, such as data points of the central wavelet (C), an amplitude of the central wavelet, a forward time constant, a backward time constant, a forward slope, a backward slope, etc. It is also possible that data representative of the actual average segments are saved. Such information can be displayed with previously determined risks of SCD, from say a month ago, and compared to see improvement or worsening of the risk of SCD. Such information can be continually, or from time to time, automatically uploaded to an external device (e.g., 102). Such an external monitoring device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

In an embodiment, a patient is alerted when a risk of SCD is sufficiently high to warrant an alert, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a high risk of SCD is assessed.

In further embodiments, a therapy can be triggered in response to assessing a high risk of SCD. One type of therapy would be for an implanted device (e.g., device 10) to stimulate the vagal nerve, in an attempt to slow down the heart rate and increase vagal tone, which is known to be generally cardioprotective. In another embodiment, the implanted device, if appropriately equipped, can deliver an appropriate drug therapy. One of ordinary skill in the art would appreciate from the above description that other types of therapies can be triggered. Similar responses can be triggered if it is determined that a patient is at imminent risk of an arrhythmia. Another appropriate response, if the patient is at imminent risk of an arrhythmia, is to start charging the capacitor(s) of an ICD, just in case there is a need to deliver shock therapy to the patient. In still another embodiment, anti-arrhythmia therapy (e.g., anti-arrhythmia pacing) can be delivered if it is determined that the patient is at risk of an immanent arrhythmia.

These are just a few examples of the types of responses that can be performed upon assessing a high risk of SCD. One of ordinary skill in the art would understand from the above description that other responses are also possible, while still being within the spirit and scope of the present invention.

These are just a few examples of how phase rectified signal averaging techniques can be used to monitor a patient's risk of SCD. Based on the description herein, those of ordinary skill in the art will appreciate that other ways are also within the spirit and scope of the present invention.

Autonomic Tone

The autonomic nervous system is a distinct system of nerves linked to the central nervous system but not under conscious voluntary control. It is responsible for non-voluntary functions, i.e., the "automatic" regulatory functions like breathing, heartbeat, digestion, etc. The autonomic nervous system is further subdivided into the sympathetic and parasympathetic systems. Similarly, autonomic tone, which is a measure of the autonomic nervous system, can be subdivided into sympathetic tone and parasympathetic tone. Measures of autonomic tone could be used to provide an indication of the progression of a disease state, such as heart failure. For example, an increase in sympathetic tone (and a decrease in parasympathetic tone) is indicative of a worsening heart failure condition. Conversely, a decrease in sympathetic tone (and an increase in parasympathetic tone) is indicative of an improving heart failure condition. As described below, embodiments of the present invention can be used to assess a patient's autonomic tone, as summarized in the flow diagram of FIG. 6.

Figure 6:
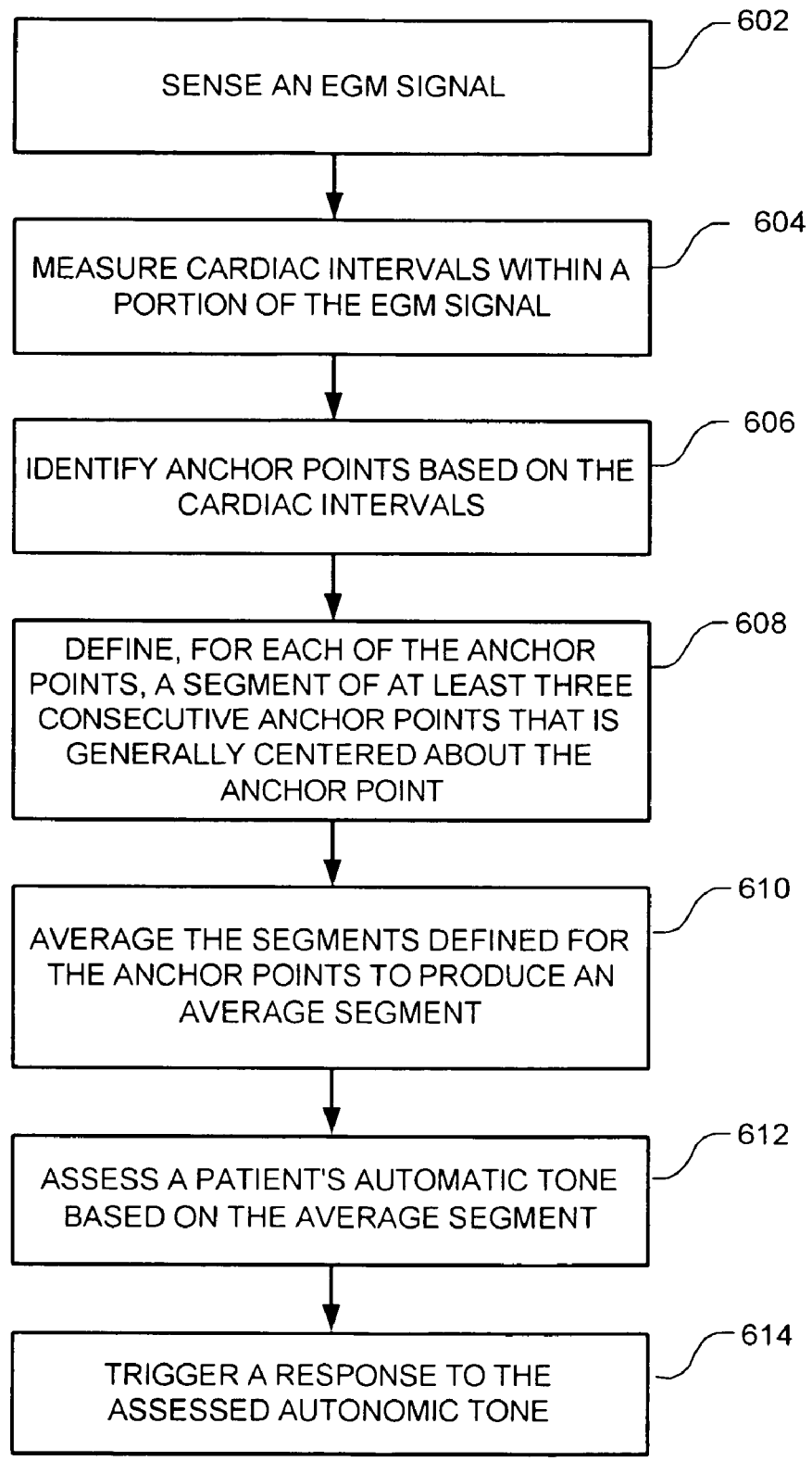
FIG. 6 is a high-level flow diagram that is useful for describing embodiments of the present invention that relate to assessing a patient's autonomic tone, which is useful e.g., for monitoring disease progression.

Referring to FIG. 6, at steps 602-610: a cardiac electrogram (EGM) signal is sensed; cardiac intervals are measured within a portion of the sensed EGM signal; anchor points are identified based on the measured cardiac intervals; for each identified anchor point, a segment is defined of at least three consecutive cardiac intervals that is generally centered about the anchor point; and the segments defined for the anchor points are averaged to produce an average segment. At step 612, a patient's autonomic tone is assessed based on the average segment. At step 614, one or more response is triggered in response to the assessed autonomic tone, if appropriate.

Steps 602-610 are essentially the same as steps 502-510, discussed above with reference to FIG. 5, and thus need not be described again in detail.

The assessing of a patient's autonomic tone at step 612 can be accomplished in various manners, as will now be explained. In accordance with certain embodiments of the present invention, a patient's autonomic tone is based on metrics of the central wavelet (C) of the average segment, where the central wavelet is the wavelet of maximum amplitude of the average segment. Exemplary techniques for characterizing the central wavelet were discussed above in the discussion of step 512 in FIG. 5. The same techniques can also be used in this embodiment. In this embodiment, if the anchor points identified at step 606 are positive anchor points (resulting in an average deceleration segment at step 610), then an increase in a metric of the central wavelet of the average deceleration segment is recognized as being indicative of an increase in parasympathetic tone, as well as a decrease in sympathetic tone; and a reduction in a metric of the central wavelet of the average deceleration segment is recognized as being indicative of a decrease in parasympathetic tone, as well as an increase in sympathetic tone. In contrast, if the anchor points identified at step 606 are negative anchor points (resulting in an average acceleration segment at step 610), then an increase in a metric of the central wavelet of the average acceleration segment is recognized as being indicative of a decrease in parasympathetic tone, as well as a increase in sympathetic tone; and a reduction in a metric of the central wavelet of the average acceleration segment is recognized as being indicative of an increase in parasympathetic tone, as well as an decrease in sympathetic tone.

Additionally or alternatively, a forward time constant and/or a backward time constant can be determined for the average segment, in a similar manner as was discussed above. The time constant (or a normalized version thereof) can then be compared to one or more threshold to specify a level of autonomic tone, which can include a level of parasympathetic and/or sympathetic tone. In this embodiment, an increase in a forward and/or backward time constant is recognized as being indicative of an increase in parasympathetic tone, as well as a decrease in sympathetic tone. Conversely, a decrease in a forward and/or backward time constant is recognized as being indicative of a decrease in parasympathetic tone, as well as an increase in sympathetic tone. For example, referring to FIGS. 4A and 4B, it can be appreciated that the forward time constant for the average segment of FIG. 4A is significantly greater than the forward time constant for the average segment of 4B, and thus that FIG. 4A is indicative of greater parasympathetic tone than FIG. 4B. Additionally, FIG. 4A is indicative of a lower sympathetic tone than FIG. 4B. This should be the same regardless whether the anchor points identified at step 606 are positive anchor points (resulting in an average deceleration segment at step 610), or negative anchor points (resulting in an average acceleration segment at step 610).

Additionally or alternatively, a forward slope and/or a backward slope can be determined for the average segment, in a similar manner as was discussed above. The slope (or a normalized version thereof) can then be compared to one or more threshold to specify a level of autonomic tone, which can include a level of parasympathetic and/or sympathetic tone. In this embodiment, an increase in a forward and/or backward slope is recognized as being indicative of an decrease in parasympathetic tone, as well as a increase in sympathetic tone. Conversely, a decrease in a forward and/or backward slope is recognized as being indicative of a increase in parasympathetic tone, as well as an decrease in sympathetic tone. For example, referring to FIGS. 4A and 4B, it can be appreciated that the forward slope for the average segment of FIG. 4A is less than the forward slope for the average segment of 4B, and thus that FIG. 4A is indicative of greater parasympathetic tone than FIG. 4B. Additionally, FIG. 4A is indicative of a lower sympathetic tone than FIG. 4B. This should be the same regardless whether the anchor points identified at step 606 are positive anchor points (resulting in an average deceleration segment at step 610), or negative anchor points (resulting in an average acceleration segment at step 610).

Each of the above metrics that are determined from an average segment (before or after normalization) can be compared to one or more threshold to determine a level of autonomic tone. For example, if a single threshold is used, then a level of parasympathetic tone can be classified as high if the metric is above the threshold, or low if the metric is below the threshold. If two thresholds are used, then the level of parasympathetic tone can be classified as high, medium or low. Of course, more thresholds can be used if the desire is to provide more levels of parasympathetic tone. Levels of sympathetic tone can be similarly assessed.

It is also within the scope of the present invention that a threshold could be specified that is indicative of an imminent risk of an arrhythmia. For example, such a threshold would be indicative of an extremely low parasympathetic tone and/or an extremely high sympathetic tone.

Since embodiments of the present invention are intended to be used with a chronically implanted device, each time the device assesses a level of autonomic tone (or measures a metric indicative of a level autonomic tone), the device can store information indicative of the level so that it can be compared with one or more previously assessed level of autonomic tone and/or one or more level of autonomic tone assessed in the future, thereby enabling the device to track changes in the patient's autonomic tone. In other words, steps 602-612 can be repeated from time to time (e.g., continually, once a day, once a week or once a month, etc.) so that changes in a patient's autonomic tone can be monitored. For a specific example, an assessed level of parasympathetic tone for the patient can be compared with a previously assessed level of parasympathetic tone for the patient to determine whether there has been an increase or a decrease in the patient's parasympathetic tone. For example, where a metric of the central wavelet of an average deceleration segment and/or the forward time constant is being used to assess the level of parasympathetic tone, an increase in the metric of the central wavelet and/or the forward time constant would be indicative of an increase in parasympathetic tone, and a decrease in the metric of the central wavelet and/or forward time constant would be indicative of a decrease in parasympathetic tone. As mentioned above, increases in parasympathetic tone (and/or decreases in sympathetic tone) can be interpreted as an improving heart failure condition, and decreases in parasympathetic tone (and/or increases in sympathetic tone) can be interpreted as a worsening heart failure condition.

As mentioned above, at step 614 one or more response can be triggered based on the assessed autonomic tone. In accordance with an embodiment of the present invention, step 614 can involve storing information related to a level of autonomic tone for later retrieval and/or transmission to a physician or other clinician. This can include, for example, storing metrics of the average segment that are indicative of levels of autonomic tone, such as data points of the central wavelet (C), a metric of the central wavelet, a forward time constant, a backward time constant, a forward slope, a backward slope, etc. It is also possible that data representative of the actual average segments are saved. Such information can be displayed with previously assessed levels of autonomic tone, from say a month ago, and compared, e.g., to see improvement or worsening of a heart failure condition. Such information can be continually, or from time to time, automatically uploaded to an external device (e.g., 102), in similar manners as were explained above.

In an embodiment, a patient is alerted when a level of parasympathetic tone is sufficiently low (and/or a level of sympathetic tone is sufficiently high) to warrant an alert, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a certain level of autonomic tone is assessed.

In further embodiments, a therapy can be triggered in response to assessing a low parasympathetic tone and/or high sympathetic tone. One type of therapy would be for an implanted device (e.g., device 10) to stimulate the vagal nerve, in an attempt to slow down the heart rate. In another embodiment, the implanted device, if appropriately equipped, can deliver an appropriate drug therapy. One of ordinary skill in the art would appreciate from the above description that other types of therapies can be triggered. Similar responses can be triggered if it is determined that a patient is at imminent risk of an arrhythmia. Another appropriate response, if the patient is at imminent risk of an arrhythmia, is to start charging the capacitor(s) of an ICD, just incase there is a need to deliver shock therapy to the patient. In still another embodiment, anti-arrhythmia therapy (e.g., anti-arrhythmia pacing) can be delivered if it is determined that the patient is at risk of an immanent arrhythmia. It is also within the scope of the present invention that levels of autonomic tone, determined using embodiments of the present invention, can be used when determining whether a patient should be upgraded to a device capable of delivering shock therapy, such as an ICD.

These are just a few examples of the types of responses that can be performed upon assessing a certain level of autonomic tone. One of ordinary skill in the art would understand from the above description that other responses are also possible, while still being within the spirit and scope of the present invention.

These are just a few examples of how phase rectified signal averaging techniques can be used to monitor a patient's autonomic tone. Based on the description herein, those of ordinary skill in the art will appreciate that other ways are also within the spirit and scope of the present invention.

Myocardial Ischemia

Myocardial ischemia is an intermediate condition in coronary artery disease during which the heart tissue is slowly or suddenly starved of oxygen and other nutrients. Eventually, the affected heart tissue will die. When blood flow is completely blocked to the heart, ischemia can lead to a myocardial infarction (also know as a "heart attack"). According to the American Heart Association, up to four million Americans may have silent ischemia and be at high risk of having a myocardial infarction with no warning. In addition, the American Heart Association estimates that nearly seven million Americans have angina pectoris, usually called angina. Therefore, by monitoring ischemia and alerting patients to seek immediate medical attention when necessary, regardless of whether the ischemia is associated with symptoms or not has relevance to patient outcomes and survival. Many ischemia monitoring algorithms detect episodes of ischemia by detecting an acute voltage shift in the ST-segment of an intracardiac electrocardiogram (ECG). It would be useful if other techniques could be used to supplant or surrogate ischemia monitoring algorithms that rely ST-segment shift analysis.

Embodiments of the present invention, which will be described below, can be used to detect myocardial ischemic events. Such ischemic events (e.g., episodes) typically last for about 30 seconds to a few minutes. Thus, to detect such relatively short events, the algorithm that is used should be repeatedly (and preferably, continually) analyzing a sensed EGM signal over relatively short time frames, as will be explained in more detail with reference to the flow diagram of FIG. 7.

Figure 7:
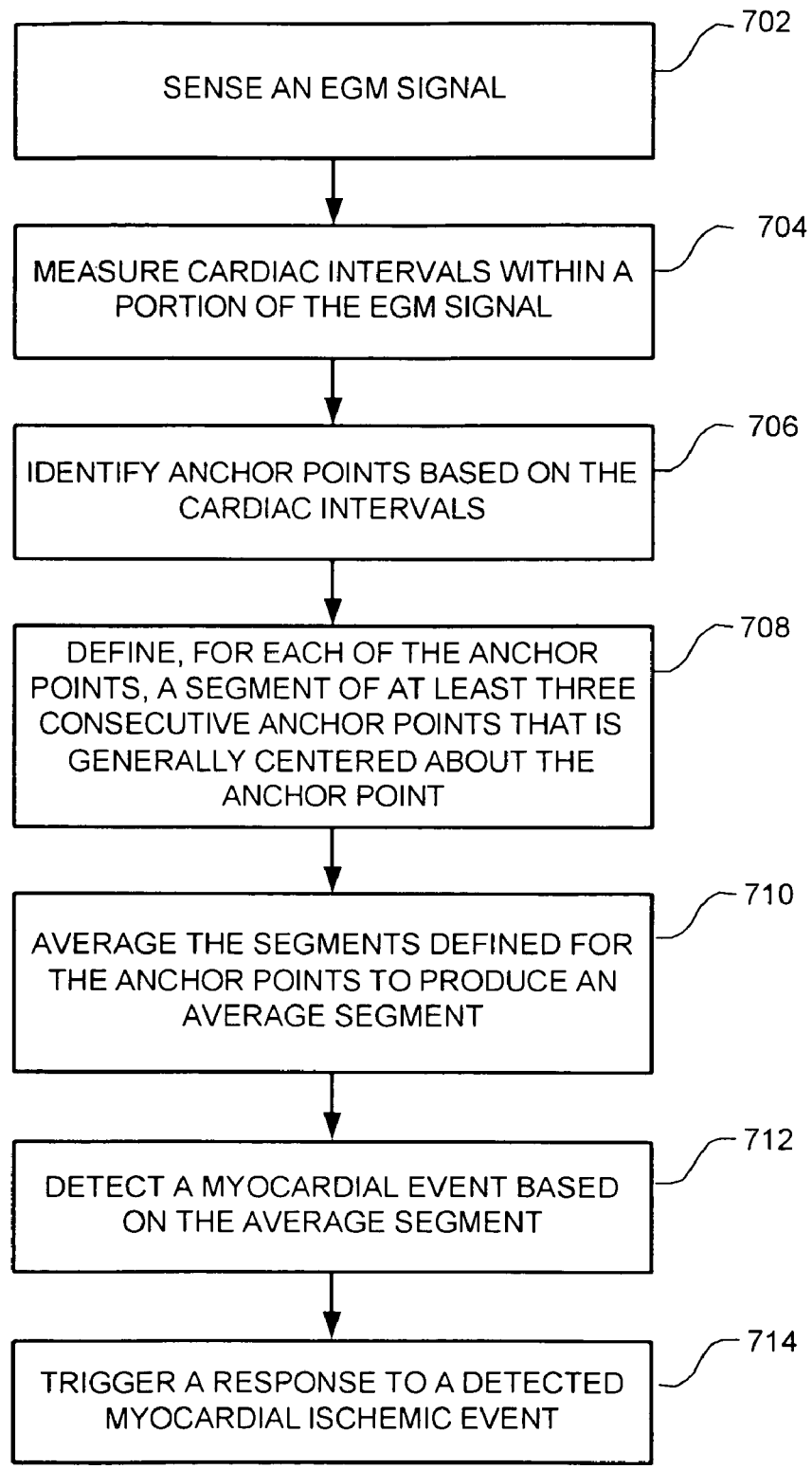
FIG. 7 is a high-level flow diagram that is useful for describing embodiments of the present invention that relate to detecting myocardial ischemic events.

Referring to FIG. 7, at steps 702 and 704, an electrogram (EGM) signal is sensed, and cardiac intervals (e.g., RR, PP or PR intervals) are measured within a portion of the sensed EGM signal. In this embodiment, the portion of the EGM signal analyzed at a time at step 704 should be short enough that relatively short myocardial ischemic events can be detected. Additionally, step 704 should be repeated frequently enough that relatively short myocardial ischemic events will not be missed. For example, it may be that step 704 is performed twice a minute, such that each time step 704 is performed cardiac intervals within a 30 second portion of an EGM signal are measured.

At steps 706 and 708, anchor points are identified based on the measured cardiac intervals, and for each identified anchor point, a segment is defined of at least three consecutive the cardiac intervals (e.g., 5 consecutive cardiac intervals) that is generally centered about the anchor point. At step 710, the segments defined for the anchor points are averaged to produce an average segment. These steps are similar to steps 506, 508 and 510 described above, and thus need not be described again in detail.

At step 712, a myocardial ischemic event is detected, if present, based on the average segment. In accordance with an embodiment of the present invention, this can be accomplished by detecting temporary decreases in a metric (e.g., amplitude) of the central wavelet of an average deceleration segment, or detecting temporary increases in a metric (e.g., amplitude) of the central wavelet of an average acceleration segment. Additionally, or alternatively, myocardial ischemic events can be detected by detecting temporary decreases in the forward and/or backward time constant of an average segment. Additionally, or alternatively, myocardial ischemic events can be detected by detecting temporary increases in the forward and/or backward slope of an average segment. Such temporary decreases or increases can be detected, e.g., by comparing a most recently determined metric (e.g., amplitude) of a central wavelet, time constant and/or slope to a corresponding baseline, with the baseline being representative of an average segment when the patient is not experiencing a myocardial ischemic event. In a specific embodiment, a myocardial ischemic event is identified (at step 712) when the measured metric of the average segment deviates from the baseline by more than a threshold. The baseline can be defined when the implantable device is implanted, or the baseline can simply be a running average of all average segments, which would essentially average out those segments corresponding to an ischemic event. Other ways for determining the baseline are also within the scope of the present invention. Additionally, other ways for detecting temporary changes in a metric (e.g., amplitude) of a central wavelet, temporary decreases in a time constant and/or temporary increases in a slope of the average segment are within the scope of the present invention. Referring back to FIGS. 4A and 4B, FIG. 4A can be representative of a baseline average segment, and FIG. 4B can be representative of an average segment indicative of a myocardial ischemic event.

At step 714, one or more response is triggered in response to detecting an ischemic event. A myocardial infarction (i.e., a heart attack) is always preceded by a myocardial ischemic event. Thus, the detection of a myocardial ischemic event may be indicative of an immanent myocardial infarction. Accordingly, in an embodiment, a patient is alerted when a myocardial ischemic event is detected, thereby allowing the patient to respond appropriately. Such an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, a myocardial infarction may be avoided, or if it does occur, the patient will be less dangerous to themselves and others if the patient is resting when the infarction occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever a myocardial ischemic event is detected.

In further embodiments, a myocardial ischemia therapy can be triggered in response to detecting an ischemic event. One type of therapy would be for an implanted device (e.g., device 10) to stimulate the vagal nerve, in an attempt to slow down the heart rate to decrease the metabolic demand. In another embodiment, the implanted device, if appropriately equipped, can deliver an appropriate drug therapy. One of ordinary skill in the art would appreciate from the above description that other types of therapies can be triggered.

These are just a few examples of the types of responses that can be performed upon detection of a myocardial ischemic event. One of ordinary skill in the art would understand from the above description that other responses are also possible, while still being within the spirit and scope of the present invention.

Figure 8:
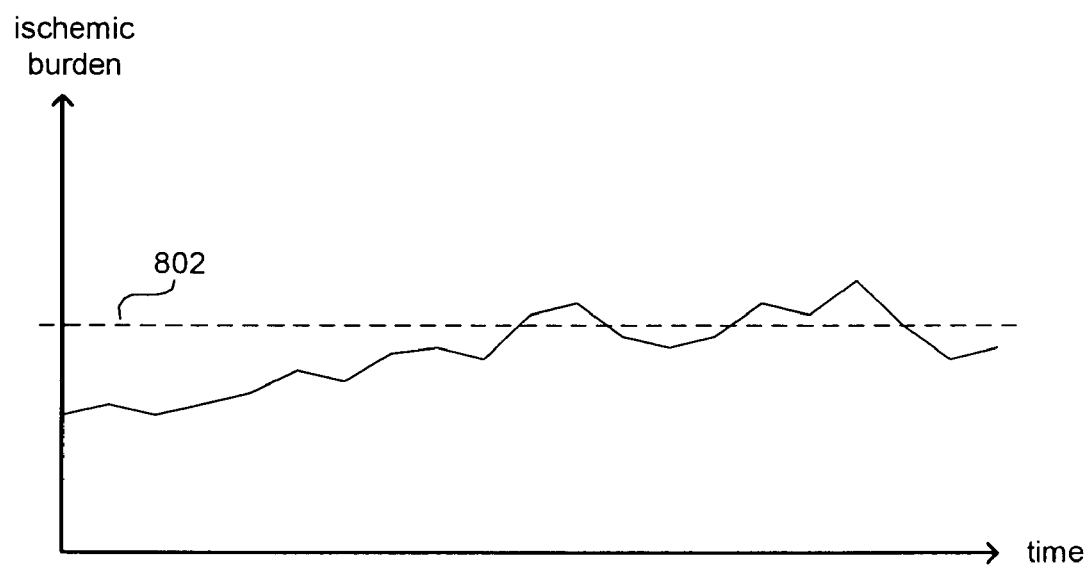
FIG. 8 is an exemplary graph of myocardial ischemic burden versus time that can be produced using embodiments of the present invention.

In accordance with an embodiment of the present invention, ischemic burden can be monitored by determining a number of ischemic events that occur during each predetermined period of time (e.g., 24 hours). By tracking ischemic burden in this manner, there can be a determination of whether ischemic burden has increased or decreased over time. Additionally, one or more ischemic burden threshold can be defined, so that one of the above responses can be triggered in response to a specific ischemic burden threshold being crossed. FIG. 8 shows an exemplary graph of ischemic burden over time, with dashed line 802 representing an exemplary threshold. It is also within the scope of the present invention that ischemic burden, determined using embodiments of the present invention, can be used when determining whether a patient should be upgraded to a device capable of delivering shock therapy, such as an ICD.

Figure 9:
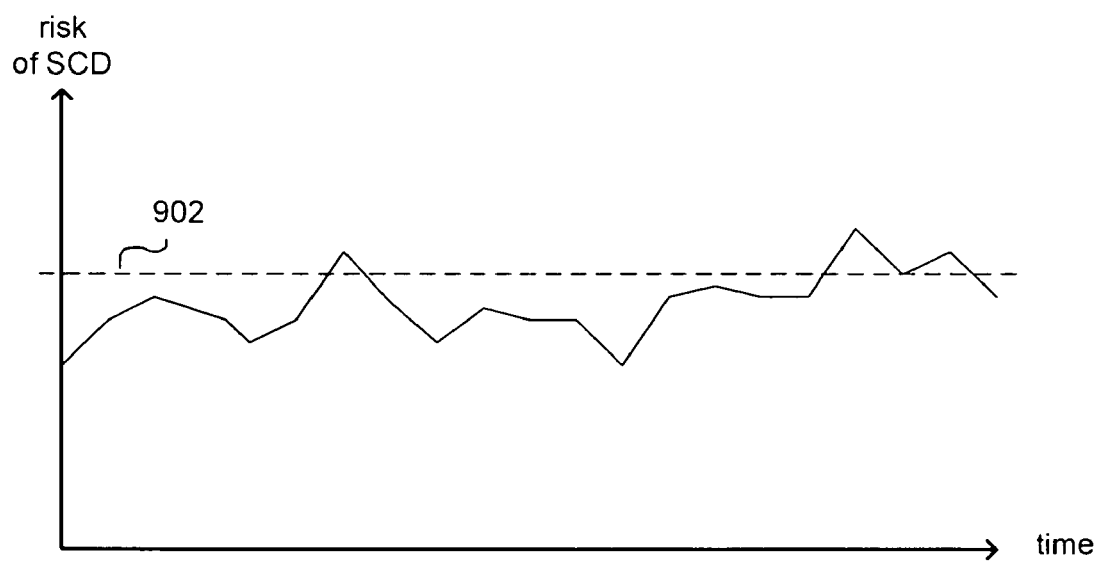
FIG. 9 is an exemplary graph of risk of SCD versus time that can be produced using embodiments of the present invention.

It is also possible to simultaneously monitor both myocardial ischemia and risk of SCD. For example, a risk of SCD over time can be monitored, e.g., as shown in FIG. 9, while ischemic burden is monitored over the same period of time, e.g., as shown in FIG. 8. Different responses can then be triggered based on both risk of SCD and ischemic burden. For example, a first response can be triggered when risk of SCD crosses its threshold, while the ischemic burden is below its threshold (e.g., represented by dashed line 902); a second response can be triggered if risk of SCD does not cross its threshold, but ischemic burden crosses its threshold; and a third response can be triggered when both risk of SCD and ischemic burden each cross their corresponding thresholds. Also, as explained above, there can be more than one threshold for each type of assessment being monitored, thereby enabling more than three different responses to potentially be triggered.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Also, it is noted that the term "base on", as used herein, means based at least in part on, unless otherwise specified.

Thus, the breadth and scope of the present invention should not be limited by any of the above-described exemplary embodiments, but should be defined only in accordance with the following claims and their equivalents.

What is claimed is:

1. For use with an implantable device, a method of performing at least one of a cardiac assessment and an autonomic assessment, comprising:
    (a) sensing a cardiac electrogram (EGM) signal using implanted electrodes;
    (b) measuring cardiac intervals within a portion of the sensed EGM signal;
    (c) identifying anchor points based on the measured cardiac intervals;
    (d) defining, for each identified anchor point, a segment of at least three consecutive said cardiac intervals that is generally centered about the anchor point;
    (e) averaging the segments defined for the anchor points to produce an average segment; and
    (f) performing at least one of a cardiac assessment and an autonomic assessment, based on the average segment.

2. The method of claim 1, wherein:
    step (c) comprises identifying each said cardiac interval that is longer than the immediately preceding cardiac interval as a positive anchor point;
    step (d) comprises defining, for each identified positive anchor point, a segment of at least three consecutive said cardiac intervals that is generally centered about the positive anchor point;
    step (e) comprises averaging the segments defined for the positive anchor points to produce an average deceleration segment; and
    step (f) comprises performing at least one of a cardiac assessment and an autonomic assessment, based on the average deceleration segment.

3. The method of claim 1, wherein:
    step (c) comprises identifying each said cardiac interval that is shorter than the immediately preceding cardiac interval as a negative anchor point;
    step (d) comprises defining, for each identified negative anchor point, a segment of at least three consecutive said cardiac intervals that is generally centered about the negative anchor point;
    step (e) comprises averaging the segments defined for the negative anchor points to produce an average acceleration segment; and
    step (f) comprises performing at least one of a cardiac assessment and an autonomic assessment, based on the average acceleration segment.

4. The method of claim 1, wherein step (f) comprises assessing a patient's autonomic tone based on the average segment.

5. The method of claim 4, wherein step (f) includes:
    determining a metric of a central wavelet of the average segment; and
    comparing the determined metric to one or more threshold to thereby assess a patient's autonomic tone.

6. The method of claim 4, wherein step (f) includes:
    determining a time constant of the average segment; and
    comparing the determined time constant to one or more threshold to thereby assess a patient's autonomic tone.

7. The method of claim 4, wherein step (f) includes:
    determining a slope of the average segment; and
    comparing the determined slope to one or more threshold to thereby assess a patient's autonomic tone.

8. The method of claim 4, further comprising:
    comparing the assessed autonomic tone for the patient with a previously assessed autonomic tone for the patient to monitor changes in autonomic tone.

9. The method of claim 4, further comprising:
    comparing the assessed autonomic tone for the patient with a threshold corresponding to an imminent risk of an arrhythmia, to determine whether the patient is at risk of an imminent arrhythmia; and
    triggering delivery of cardiac therapy in response to a determination that the patient is at risk of an imminent arrhythmia.

10. The method of claim 4, wherein:
    step (c) comprises identifying each said cardiac interval that is longer than the immediately preceding cardiac interval as a positive anchor point;
    step (d) comprises defining, for each identified positive anchor point, a segment of at least three consecutive said cardiac intervals that is generally centered about the positive anchor point;
    step (e) comprises averaging the segments defined for the positive anchor points to produce an average deceleration segment; and
    step (f) includes at least one of the following, based on the average deceleration segment,
    recognizing a decrease in a metric of a central wavelet of the average deceleration segment as being indicative of a decrease in parasympathetic tone;
    recognizing a decrease in a metric of a central wavelet of the average deceleration segment as being indicative of an increase in sympathetic tone;
    recognizing an increase in a metric of a central wavelet of the average deceleration segment as being indicative of an increase in parasympathetic tone; and
    recognizing an increase in a metric of a central wavelet of the average deceleration segment as being indicative of a decrease in sympathetic tone.

11. The method of claim 4, wherein:
    step (c) comprises identifying each said cardiac interval that is shorter than the immediately preceding cardiac interval as a negative anchor point;
    step (d) comprises defining, for each identified negative anchor point, a segment of at least three consecutive said cardiac intervals that is generally centered about the negative anchor point;
    step (e) comprises averaging the segments defined for the negative anchor points to produce an average acceleration segment; and
    step (f) includes at least one of the following, based on the average acceleration segment,
    recognizing an increase in a metric of a central wavelet of the average acceleration segment as being indicative of a decrease in parasympathetic tone;
    recognizing an increase in a metric of a central wavelet of the average acceleration segment as being indicative of an increase in sympathetic tone;
    recognizing a decrease in a metric of a central wavelet of the average acceleration segment as being indicative of an increase in parasympathetic tone; and
    recognizing a decrease in a metric of a central wavelet of the average acceleration segment as being indicative of a decrease in sympathetic tone.

12. The method of claim 4, wherein step (f) includes at least one of the following:
    recognizing a decrease in a time constant of the average segment as being indicative of a decrease in parasympathetic tone;

recognizing a decrease in a time constant of the average segment as being indicative of an increase in sympathetic tone;

recognizing an increase in a time constant of the average segment as being indicative of an increase in parasympathetic tone; and recognizing an increase in a time constant of the average segment as being indicative of a decrease in sympathetic tone.

13. The method of claim 4, wherein step (f) includes at least one of the following:
recognizing a decrease in a slope of the average segment as being indicative of an increase in parasympathetic tone;
recognizing a decrease in a slope of the average segment as being indicative of a decrease in sympathetic tone;
recognizing an increase in a slope of the average segment as being indicative of a decrease in parasympathetic tone; and
recognizing an increase in a slope of the average segment as being indicative of an increase in sympathetic tone.

14. The method of claim 4, comprising repeating steps (a) through (f) over time to monitor changes in the patient's autonomic tone.

15. The method of claim 1, wherein step (f) comprises assessing a patient's risk of sudden cardiac death (SCD) based on the average segment.

16. The method of claim 15, further comprising:
comparing the assessed risk of SCD for the patient with a previously assessed risk of SCD for the patient to determine whether there has been an increase or a decrease in the patient's risk of SCD.

17. The method of claim 15, further comprising:
comparing the assessed risk of SCD for the patient with a threshold corresponding to an imminent risk of an arrhythmia, to determine whether the patient is at risk of an imminent arrhythmia; and
triggering delivery of cardiac therapy in response to a determination that the patient is at risk of an imminent arrhythmia.

18. The method of claim 15, wherein:
step (c) comprises identifying each said cardiac interval that is longer than the immediately preceding cardiac interval as a positive anchor point;
step (d) comprises defining, for each identified positive anchor point, a segment of at least three consecutive said cardiac intervals that is generally centered about the positive anchor point;
step (e) comprises averaging the segments defined for the positive anchor points to produce an average deceleration segment; and
step (f) includes at least one of the following, based on the average deceleration segment,
recognizing a decrease in a metric of a central wavelet of the average deceleration segment as being indicative of an increase in risk of SCD; and
recognizing an increase in a metric of a central wavelet of the average deceleration segment as being indicative of a decrease in risk of SCD.

19. The method of claim 15, wherein:
step (c) comprises identifying each said cardiac interval that is shorter than the immediately preceding cardiac interval as a negative anchor point;
step (d) comprises defining, for each identified negative anchor point, a segment of at least three consecutive said cardiac intervals that is generally centered about the negative anchor point;

step (e) comprises averaging the segments defined for the negative anchor points to produce an average acceleration segment; and
step (f) includes at least one of the following, based on the average deceleration segment:
recognizing a decrease in a metric of a central wavelet of the average acceleration segment as being indicative of a decrease in risk of SCD; and
recognizing an increase in a metric of a central wavelet of the average acceleration segment as being indicative of an increase in risk of SCD.

20. The method of claim 15, wherein step (f) includes at least one of the following:
recognizing a reduction in a time constant of the average segment as being indicative of an increase in risk of SCD; and
recognizing an increase in a time constant of the average segment as being indicative of a reduction in risk of SCD.

21. The method of claim 15, wherein step (f) includes at least one of the following:
recognizing a decrease in a slope of the average segment as being indicative of a decrease in risk of SCD; and
recognizing an increase in a slope of the average segment as being indicative of an increase in risk of SCD.

22. The method of claim 15, comprising repeating steps (a) through (f) over time to monitor changes in the patient's risk of SCD.

23. The method of claim 1, wherein step (f) comprises detecting a myocardial ischemic event based on the average segment.

24. The method of claim 23, wherein:
step (c) comprises identifying each said cardiac interval that is longer than the immediately preceding cardiac interval as a positive anchor point;
step (d) comprises defining, for each identified positive anchor point, a segment of at least three consecutive said cardiac intervals that is generally centered about the positive anchor point;
step (e) comprises averaging the segments defined for the positive anchor points to produce an average deceleration segment; and
step (f) includes recognizing a temporary decrease in a metric of a central wavelet of the average deceleration segment as being indicative of a myocardial ischemic event.

25. The method of claim 23, wherein:
step (c) comprises identifying each said cardiac interval that is shorter than the immediately preceding cardiac interval as a negative anchor point;
step (d) comprises defining, for each identified negative anchor point, a segment of at least three consecutive said cardiac intervals that is generally centered about the negative anchor point;
step (e) comprises averaging the segments defined for the negative anchor points to produce an average acceleration segment; and
step (f) includes recognizing a temporary increase in a metric of a central wavelet of the average acceleration segment as being indicative of a myocardial ischemic event.

26. The method of claim 23, wherein step (f) includes recognizing a temporary decrease in a time constant of the average segment as being indicative of a myocardial ischemic event.

27. The method of claim 23, wherein step (f) includes recognizing a temporary increase in a slope of the average segment as being indicative of a myocardial ischemic event.

28. The method of claim 23, comprising repeating steps (a) through (f) over time and assessing an ischemic burden based on identified myocardial ischemic events.

29. An implantable device for assessing autonomic tone, comprising:
- implantable electrodes for sensing a cardiac electrogram (EGM) signal;
- means for measuring cardiac intervals within a portion of the sensed EGM signal;
- means for identifying anchor points based on the measured cardiac intervals;
- means for defining, for each identified anchor point, a segment of at least three consecutive said cardiac intervals that is generally centered about the anchor point;
- means for averaging the segments defined for the anchor points to produce an average segment; and
- means for assessing autonomic tone based on the average segment.

30. An implantable device for assessing a risk of sudden cardiac death (SCD), comprising:
- implantable electrodes for sensing a cardiac electrogram (EGM) signal;
- means for measuring cardiac intervals within a portion of the sensed EGM signal;
- means for identifying anchor points based on the measured cardiac intervals;
- means for defining, for each identified anchor point, a segment of at least three consecutive said cardiac intervals that is generally centered about the anchor point;
- means for averaging the segments defined for the anchor points to produce an average segment; and
- means for assessing risk of SCD based on the average segment.

31. An implantable device for detecting myocardial ischemic events, comprising:
- implantable electrodes for sensing a cardiac electrogram (EGM) signal;
- means for measuring cardiac intervals within a portion of the sensed EGM signal;
- means for identifying anchor points based on the measured cardiac intervals;
- means for defining, for each identified anchor point, a segment of at least three consecutive said cardiac intervals that is generally centered about the anchor point;
- means for averaging the segments defined for the anchor points to produce an average segment; and
- means for detecting a myocardial ischemic event based on the average segment.

* * * * *